(12) United States Patent
Bolton et al.

(10) Patent No.: US 9,828,319 B2
(45) Date of Patent: Nov. 28, 2017

(54) PROCESS FOR THE ACID-CATALYSED DEHYDRATION OF ETHANOL

(71) Applicant: Technip E&C Limited, Milton Keynes (GB)

(72) Inventors: Leslie William Bolton, Middlesex (GB); Nigel Stewart Brown, East Yorkshire (GB); Lewis Adam Heptonstall, East Yorkshire (GB); Andrew John Hogben, East Yorkshire (GB); Susan Elizabeth Little, Middlesex (GB); Stephen James Smith, East Yorkshire (GB)

(73) Assignee: Technip E&C Limited, Milton Keynes (GB)

( * ) Notice: Subject to any disclaimer, the term of this patent is extended or adjusted under 35 U.S.C. 154(b) by 0 days.

(21) Appl. No.: 15/108,234

(22) PCT Filed: Dec. 19, 2014

(86) PCT No.: PCT/EP2014/078853
§ 371 (c)(1),
(2) Date: Jun. 24, 2016

(87) PCT Pub. No.: WO2015/097100
PCT Pub. Date: Jul. 2, 2015

(65) Prior Publication Data
US 2016/0326080 A1    Nov. 10, 2016

(30) Foreign Application Priority Data
Dec. 24, 2013 (EP) .................................... 13199602

(51) Int. Cl.
| C07C 41/09 | (2006.01) |
| C07C 1/24 | (2006.01) |
| C07C 29/80 | (2006.01) |
| C07C 29/82 | (2006.01) |
| C07C 41/06 | (2006.01) |

(52) U.S. Cl.
CPC ................ C07C 41/09 (2013.01); C07C 1/24 (2013.01); C07C 29/80 (2013.01); C07C 29/82 (2013.01); C07C 41/06 (2013.01); C07C 2529/06 (2013.01)

(58) Field of Classification Search
CPC ......... C07C 29/80; C07C 29/82; C07C 41/06; C07C 1/24; C07C 41/09; C07C 2529/06
See application file for complete search history.

(56) References Cited

U.S. PATENT DOCUMENTS

| 4,018,562 A | 4/1977 | Parks et al. |
| 5,415,741 A | 5/1995 | Berg |
| 6,770,790 B1 | 8/2004 | Li et al. |

FOREIGN PATENT DOCUMENTS

| EP | 0053917 A1 | 6/1982 |
| EP | 1176132 A1 | 1/2002 |
| GB | 2373856 A | 10/2002 |
| WO | WO-1997/045392 A1 | 12/1997 |
| WO | WO-2008/062157 A1 | 5/2008 |
| WO | WO-2008/138775 A1 | 11/2008 |
| WO | WO-2009/098262 A1 | 8/2009 |
| WO | WO-2010/060981 A1 | 6/2010 |
| WO | WO-2011/089235 A1 | 7/2011 |

OTHER PUBLICATIONS

International Search Report issued in International Application No. PCT/EP2014/078853, dated Oct. 14, 2015.

*Primary Examiner* — Rosalynd Keys
(74) *Attorney, Agent, or Firm* — Porzio, Bromberg & Newman P.C.

(57) ABSTRACT

A process for the acid-catalyzed dehydration of ethanol, the process comprising the steps of distilling an ethanol feedstock (101) comprising at least one nitrogen-containing contaminant to form an overhead stream (102) and a bottom stream comprising ethanol (103), wherein the distillation has a reflux ratio of at least 20:1; and reacting the bottom stream in the presence of an acid catalyst to form a product stream comprising ethylene.

25 Claims, 1 Drawing Sheet

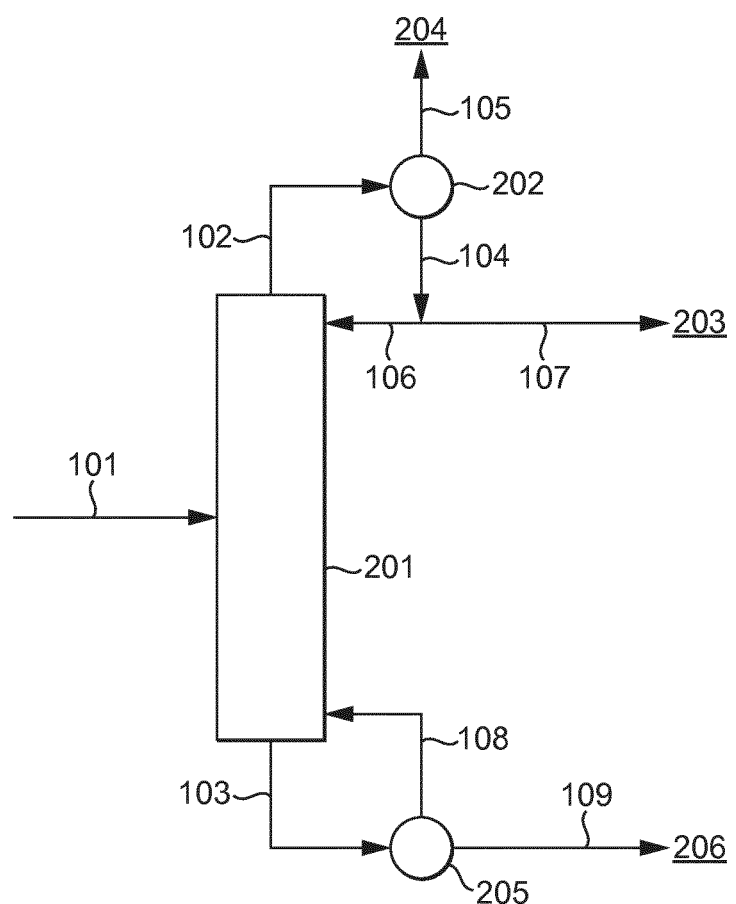

PROCESS FOR THE ACID-CATALYSED DEHYDRATION OF ETHANOL

The present invention relates to processes for the acid-catalysed dehydration of ethanol, for example a process for producing ethylene and/or diethyl ether by the vapour phase dehydration of ethanol using a heteropolyacid catalyst such as silicotungstic acid.

BACKGROUND OF THE INVENTION

Ethanol is widely used commercially as a gasoline additive or as a fuel per se, as a solvent, as a germicide, as an antifreeze, as a component in the food and beverage industry, and as a chemical feedstock. It is particularly useful as a feedstock for acid-catalysed reactions such as the dehydration to ethylene. See e.g. WO 2008/138775 which discloses a process for the dehydration of one or more alcohols comprising contacting the one or more alcohols with a supported heteropolyacid catalyst in the presence of one or more ethers; and WO 2008/062157 which discloses a heteropolyacid catalyst and the use thereof in a process for the production of olefins from oxygenates.

Ethanol is of increasing significance as a chemical feedstock, since it is readily obtainable from biological sources, in particular by the fermentation of sugars and/or biomass. Ethanol from biological sources, so-called bio-ethanol, thus provides one way of reducing the dependence on crude oils for fuel uses and as chemical feedstocks.

Ethanol, particularly bio-ethanol (or ethanol obtained by fermentation) typically contains low levels of nitrogen-containing contaminants. One possible source of nitrogen-containing contaminants may be ammonia which may be introduced during the fermentation stage. Once in the process, the ammonia can react with ethanol and other impurities to form a variety of nitrogen-containing compounds.

The presence of nitrogen-containing contaminants in ethanol is undesirable since these compounds may interfere with subsequent chemical processing in which the ethanol is used as a feedstock. For example, nitrogen-containing contaminants, which may be volatile nitrogen compounds such as acetonitrile and ammonia, and particularly acetonitrile, can poison, deactivate or otherwise interfere (e.g. act as a precursor to a catalyst poison) with a number of catalysts which may be used in the processing of alcohol feedstocks, for example by neutralising acidic sites on heterogeneous acidic catalysts. This may lead to a loss of process efficiency and a need to undesirably replace the catalyst more frequently. Approaches have been taken to reduce the level of acetonitrile in ethanol feedstocks, with such approaches including aqueous extraction, sacrificing acid and adsorption.

WO 1997/045392 discloses a process for the production of ethers in which deactivation of an acidic ion-exchange resin etherification catalyst is reduced by separating nitriles from an olefin feedstock by aqueous extraction. The nitriles are subsequently separated into an alcohol phase and hydrogenated to form amines which are more easily separable from the alcohol phase by fractionation.

EP 1 176 132 A1 discloses a process for preparing ethers comprising reacting an alcohol and an olefin in the presence of an acidic catalyst. Excess alcohol is recycled to the reaction zone together with nitrile compounds originating from the olefin feed. To avoid accumulation of nitriles in the system and deactivation of the catalyst, the excess alcohol comprising nitrile compounds is contacted in the liquid phase with a solid acid prior to being recycled to the reaction zone. It is reported that this reduces the level of nitriles in the recycled alcohol stream by at least 50%.

WO 2010/060981 discloses a process for the purification of an alcohol in the course of a process for the preparation of olefins by acid-catalysed dehydration of the alcohol, the process comprising contacting the alcohol with one or more adsorbent materials. It is disclosed in WO 2010/060981 that while ammonia and amines can be adsorbed, nitrile impurities such as acetonitriles must be hydrogenated to provide modified impurities which are more readily adsorbed. Thus, according to WO 2010/060981, the alcohol feed is subjected to a hydrogenation step prior to contacting the alcohol with the one or more adsorbent materials. The Examples of WO 2010/060981 teach the removal of basic compounds from bio-ethanol by adsorption on a sulfonic acid resin at ambient temperature and pressure.

However, such means to reduce the level of acetonitrile are relatively inefficient (e.g. requiring additional process steps or relatively poor reduction in acetonitrile level) and lead to other disadvantages such as a need to dispose of the aqueous extract or the need to replace the material onto which contaminants are adsorbed.

Accordingly, there remains a need for a means to remove nitrogen-containing contaminants including volatile nitrogen compounds (especially acetonitrile) from an ethanol feedstock while avoiding the drawbacks of the prior approaches, such as the aforementioned inefficiencies and need to replace the means being employed, to reduce the level of volatile nitrogen compounds in an ethanol feedstock.

SUMMARY OF THE INVENTION

In a first aspect, the present invention relates to a process for the acid-catalysed dehydration of ethanol, the process comprising the steps of:
  (a) distilling an ethanol feedstock (101) comprising at least one nitrogen-containing contaminant to form an overhead stream (102) and a bottom stream comprising ethanol (103), wherein the distillation has a reflux ratio of at least 20:1, and
  (b) reacting the bottom stream in the presence of an acid catalyst to form a product stream comprising ethylene and/or diethyl ether.

Alternatively described, the present invention relates to a process for the acid-catalysed dehydration of ethanol, the process comprising the steps of:
  (i) distilling an ethanol feedstock (101) comprising at least one nitrogen-containing contaminant to form an overhead stream (102) and a bottom stream comprising ethanol (103),
  (ii) condensing the overhead stream to form a condensed stream (104) and a gaseous stream (105),
  (iii) returning a first portion of the condensed stream to step (i) as a reflux liquid stream (106) and taking off a second portion of the condensed stream as a distillate stream (107), wherein the reflux ratio, being the rate of the reflux liquid stream returned to the rate of the distillate stream taken off, is at least 20:1; and
  (iv) reacting the bottom stream in the presence of an acid catalyst to form a product stream comprising ethylene and/or diethyl ether.

In a second aspect, the present invention relates to a process for the preparation of an ethanol feedstock for the acid-catalysed dehydration of ethanol to ethylene, the process comprising the step of distilling an ethanol feedstock comprising at least one nitrogen-containing contaminant wherein the distillation has a reflux ratio of at least 20:1 and the ethanol feedstock exits the distilling step in a bottom stream.

In a third aspect, the present invention relates to uses of processes according to the first aspect to react a nitrogen-containing contaminant-depleted, preferably acetonitrile-depleted, ethanol feedstock in the presence of an acid catalyst, and to react a non-condensable gas depleted, preferably an oxygen, carbon dioxide, carbon monoxide and/or nitrogen depleted, ethanol feedstock in the presence of an acid catalyst.

In a fourth aspect, the present invention relates to products obtainable, preferably obtained, from processes according to the first or second aspect.

BRIEF DESCRIPTION OF THE DRAWING

FIG. 1 shows a schematic representation of a process according to the present invention.

DETAILED DESCRIPTION OF THE INVENTION

In a first aspect, the present invention provides processes for the acid-catalysed dehydration of ethanol and particularly to methods involving the purification of the ethanol feedstock before reacting it in the presence of an acid catalyst. The ethanol feedstock used in the present process can in principle be from any source, but preferably comprises bio-ethanol or is a bio-ethanol feedstock.

As used herein, the term "ethanol feedstock" refers to a composition which comprises at least about 50% ethanol. Preferably, an ethanol feedstock to be treated according to the process of the present invention is an ethanol feedstock comprising at least about 70 wt % ethanol, more preferably at least about 80 wt % ethanol, even more preferably at least about 85 wt % ethanol and even more preferably still at least about 90% ethanol. In some embodiments, the ethanol feedstock is, or comprises, bio-ethanol.

The ethanol feedstock may additionally comprise an inert component, wherein said inert component is any component which does not react with ethanol or adversely affect the distillation step under the conditions used and would not adversely affect a process for the acid-catalysed reaction of ethanol, e.g. the dehydration of ethanol to ethylene and/or diethyl ether. By way of example, the inert component may be selected from saturated hydrocarbon compounds having from 1 to about 10 carbon atoms, napthenes, and inert gases such as nitrogen.

The ethanol feedstock may comprise a single type of alcohol (i.e. just ethanol), or it may comprise a mixture of two or more different alcohols (e.g. ethanol plus at least one further alcohol).

In some particular embodiments, the alcohols present in the ethanol feedstock are substantially ethanol, for example at least about 95 wt % of the alcohols present in the ethanol feedstock is ethanol, preferably at least about 98 wt %, such as at least about 99 wt % or at least about 99.5 wt %, of the alcohols present in the ethanol feedstock is ethanol.

In some embodiments, the ethanol feedstock comprises ethanol produced from a biological source (bio-ethanol), for example by fermentation of biomass and/or a derivative thereof. The term "biomass" as used herein refers to any biological source of a carbohydrate which may be converted to an alcohol by fermentation of the biomass directly or fermentation of a derivative of the biomass; for example biological sources of sugars, starches and cellulose. For instance, bio-ethanol may be obtained by the fermentation of sugars from sources such as sugar beet, sugar cane, molasses or corn syrup. As such, bio-ethanol may be obtained by fermentation of feedstocks derived from sugar cane, such as sugar cane molasses and sugar cane juice; sugar beet, such as sugar beet molasses and sugar beet juice; cereal crops, such as corn or wheat derived feedstocks like corn syrup; and lignocellulosic materials, such as fast growing grasses or "energy grasses".

In some embodiments of the present invention, the ethanol feedstock may comprise water. For example, the ethanol feedstock may be a hydrous ethanol composition, e.g. one which has not been dried beyond the ethanol-water azeotrope composition. Such hydrous ethanol compositions may be the raw or crude ethanol composition which results from the production of an ethanol product which has been obtained by the fermentation of biomass without further subjecting the obtained ethanol to a dewatering step that dries the composition beyond the ethanol-water azeotrope. Such hydrous ethanol compositions may contain an amount of water which is equal to or greater than the amount of water which is determined by the azeotrope of the ethanol-water composition. A hydrous ethanol composition includes also those to which water has been added, for example, an ethanol or bio-ethanol composition to which from about 0.01% to about 5% water, preferably from about 0.5% to about 4%, more preferably from about 1% to about 3% and even more preferably from about 1.5% to about 2.5%, such as about 2%, water has been added, all by weight of the ethanol composition. Additionally or alternatively, the ethanol feedstock may comprise an organic acid such as acetic acid. The acetic acid present in the ethanol feedstock (or the amount of acetic added to the ethanol feedstock) may be from about 10 ppb to about 1000 ppm, preferably from about 1 ppm to about 500 ppm, more preferably from about 10 ppm to about 300 ppm, even more preferably from about 50 ppm to about 200 ppm, and even more preferably still from about 70 ppm to about 150 ppm, such as about 100 ppm, by weight. Any of the amounts of water added disclosed above may be added in combination with the acetic acid ranges described above, or differing levels of water may be added, such as from about 0.7% to about 10%, preferably from about 1.2% to about 7%, and more preferably from about 1.8% to about 5%, by weight. A distillation comprising additional water and/or organic acid (especially acetic acid) may be operated without adherence to the reflux ratios described herein.

Alternatively, the ethanol feedstock may be an anhydrous ethanol composition, i.e. composed of anhydrous alcohol. Such anhydrous ethanol compositions may contain an amount of water which is less than the amount of water which is determined by the azeotrope of the ethanol-water composition. For example, by weight, an anhydrous ethanol composition may be at least about 95% ethanol, preferably at least about 98% ethanol, more preferably at least about 99% ethanol and even more preferably at least about 99.5% ethanol. Although termed "anhydrous," it is understood and accepted that the remainder of the composition besides the ethanol may comprise water, or be substantially water.

The concentration of nitrogen-containing contaminants in the ethanol feedstock to be treated according to the process of the present invention will generally be at a level which is detrimental to the performance of an acid catalyst, such as a supported heteropolyacid catalyst. In this disclosure, concentrations of nitrogen-containing contaminants are usually reported as parts per million by weight (ppmw) of the total nitrogen content of said nitrogen-containing contaminants.

References herein to ppmw of nitrogen shall be interpreted as ppmw of nitrogen in the form of nitrogen-containing contaminants. The ranges provided below may apply to the sum for all nitrogen-containing contaminants, to a subset of them, or to a particular example, such as acetonitrile. Thus, the ethanol feedstock to be treated according to the process of the invention may comprise over about 0.05 ppmw of nitrogen, preferably at least 0.2 ppmw of nitrogen, more preferably at least about 0.25 ppmw of nitrogen, more preferably at least about 0.3 ppmw of nitrogen, still more preferably at least about 0.4 ppmw of nitrogen, and most preferably at least about 0.5 ppmw of nitrogen. For instance, the ethanol feedstock to be treated according to the process of the invention may comprise at least about 0.6 ppmw, at least about 0.7 ppmw, at least about 0.8 ppmw, at least about 0.9 ppmw or at least about 1.0 ppmw of nitrogen.

Higher levels of nitrogen-containing contaminants may appear in ethanol feedstocks. Thus, concentrations of nitrogen-containing contaminants of over about 100 ppmw of nitrogen, such as over about 200 ppmw of nitrogen, over about 500 ppmw of nitrogen, or even over about 1000 ppmw of nitrogen, are readily treatable by the process of the present invention. However, to provide a lower nitrogen-containing contaminant level overall and to improve the performance of optional further purification steps such as adsorption it may be preferable that the ethanol feedstock comprises about 50 ppmw or less of nitrogen, more preferably about 25 ppmw or less of nitrogen, more preferably about 10 ppmw or less of nitrogen, more preferably about 8 ppmw or less of nitrogen, for instance about 6 ppmw or less of nitrogen, about 4 ppmw or less of nitrogen, or about 2 ppmw or less of nitrogen. The levels of nitrogen-containing contaminants in the ethanol feedstock provided above may be applicable at the beginning of an overall process involving the distillation of the present invention (e.g. one comprising further purification steps such as adsorption) or may be applicable specifically prior to the distillation step. Thus, depending upon the initial concentration of nitrogen in the ethanol feedstock to be treated, it may be desirable to subject ethanol feedstocks comprising very high levels of nitrogen-containing contaminants to a pre-treatment step to reduce the level of nitrogen-containing contaminants. Such a pre-treatment may be carried out by any suitable technique, for instance by contacting the ethanol feedstock with an adsorbent as discussed below.

The concentration of nitrogen-containing contaminants in the ethanol feedstock to be treated according to the process of the invention may be determined by any suitable analytical technique known to persons of skill in the art. Suitable techniques include gas chromatography in conjunction with a nitrogen/phosphorus detector (GC-NPD), chemiluminescence methods and ion exchange chromatography. It has been found that GC-NPD is a particularly effective technique for observing individual nitrogen-containing species in the ethanol feedstock. The use of a nitrogen/phosphorus detector provides significantly enhanced signal strength for nitrogen compounds in comparison to carbon species (approximately $10^4$ enhancement). As a result, nitrogen compounds are clearly visible in the GC chromatogram along with the signals for the alcohol and in some cases the corresponding dialkyl ether.

A suitable chemiluminescence technique may involve vaporising and oxidizing an ethanol feedstock, measuring the concentration of nitrogen oxides in the vaporized and oxidized ethanol feedstock by chemiluminescence and hence determining the concentration of nitrogen atoms in the ethanol feedstock from the measured concentration of nitrogen oxides. Such techniques are described in further detail in U.S. Pat. No. 4,018,562 and GB 2373856.

The nitrogen-containing contaminants may include a number of different types of nitrogen-containing compounds, such as nitrogen-containing contaminants with a lower boiling point than ethanol, for instance volatile nitrogen compounds. Examples of nitrogen-containing contaminants include nitriles (i.e. compounds containing one or more nitrile moiety, such as acetonitrile), amines (i.e. compounds containing one or more amine moiety, such as ammonia, methylamine, ethylamine, dimethylamine, diethylamine, triethylamine, trimethylamine, ethanolamine), ammonium cations, amides, imides and mixtures thereof; additionally, more complex and heterocyclic nitrogen-containing compounds, such as azines, diazines, pyrroles, diazoles, triazoles, tetrazoles and mixtures thereof, and more complex molecules containing one or more different nitrogen-containing moieties and optional other functional groups, such as amino acids, may also be present in the ethanol feedstock. Nitriles have low basicity due to the sp hybridization of the nitrogen atom which places the electron density of the nitrogen lone-pair close to the nitrogen nucleus, thus making the lone-pair relatively unreactive. Consequently, nitriles such as acetonitrile in particular pass through acidic adsorbents with substantially no adsorption at the concentrations typical in ethanol feedstocks, especially bio-ethanol. Nonetheless, nitriles are found to be capable of quantitatively deactivating acidic catalysts used for alcohol dehydration processes. It has previously been proposed to carry out a pre-treatment step to convert nitriles to amines by hydrogenation, as amines are more readily adsorbed. By employing the process of the present invention, a reduction in the concentration of all nitrogen-containing compounds, especially nitriles such as acetonitrile, to very low levels is achievable without the need to pretreat the ethanol feedstock to chemically modify nitrile contaminants. As it appears throughout this document, the term "nitrogen-containing contaminants" may be taken to refer to all nitrogen-containing contaminants, any subset of them (e.g. combination of those cited above), or any particular one (for example acetonitrile), as if simply replaced with the alternative terminology.

The processes according to the invention comprise the step of distilling an ethanol feedstock with a reflux ratio of at least about 20:1 to form an overhead stream and a bottom stream. The distillation may be performed in a conventional distillation column with a number of stages (e.g. ideal stages) commensurate with the reflux ratio required, for example between about 5 and about 50 ideal separation stages. As the column typically removes lighter boiling components, so, without being bound by theory, the feed point should generally be in the lower part of the column. While generally distillation columns have a reboiler, in this instance if the feed is pre-heated to contain at least a mixture of liquid and vapour this may be sufficient to provide enough heat to drive the required separation within the column. The column is also usually fitted with an overhead condenser to condense the overhead vapour to provide the liquid reflux stream and to optionally allow the separation of the non-condensable components.

The respective boiling points of acetonitrile (81.48° C.) and ethanol (78.37° C.) at atmospheric pressure are such that their separation by distillation would be expected to be extremely difficult under normal conditions (only about 3° C. difference in boiling point) and even if achieved, it is the ethanol that would be expected to be boiled off and leave the distillation column overhead, thus making an inefficient process requiring a lot of energy as the larger fraction of the feedstock (rather than the smaller impurity fraction) is being boiled off. However, the applicants have unexpectedly found that operating a distillation according to the present invention enables the separation of acetonitrile from the ethanol feedstock with distillate comprising acetonitrile (i.e. the acetonitrile is the distillate, or at least a portion of the distillate, or is at a higher concentration in the distillate than the treated ethanol or distillation bottoms), thus reducing the level in the ethanol stream used for further process steps, and therefore reducing the extent of catalyst deactivation when subsequent process steps utilise an acid catalyst. Without wishing to be bound by theory, the applicants have recognised that an azeotropic mixture forms between ethanol (55 mol %) and acetonitrile (45 mol %) with a boiling point (72.8° C.) which is lower than that of ethanol (78.31° C.) (the quoted proportions and boiling points here being at atmospheric pressure). Surprisingly, this azeotropic effect is available even at very low concentrations of acetonitrile and thus enables removal of the nitrogen-containing contaminant by distillation overhead, reducing the energy required for the process step. As the level of acetonitrile is typically low (such as up to about 10 ppm) in feedstock ethanol, the quantity of ethanol lost through the distillation is also small. Also surprisingly, the applicants have found that a similar azeotropic effect also enables separation in the presence of water, i.e. an ethanol/acetonitrile/water azeotrope (boiling point 72.7° C. at atmospheric pressure) and an ethanol/water azeotrope (boiling point 78.2° C. at atmospheric pressure) are surprisingly able to facilitate acetonitrile separation even at low concentrations of acetonitrile. Details of the boiling points of major components in a typical ethanol feedstock and azeotropes appear in Table 1 below (all temperatures for distillation at atmospheric pressure, i.e. 1 bara).

TABLE 1

Boiling points of components and the azeotropes associated with components typically found in ethanol feedstock.

| | |
|---|---|
| Ethanol | 78.31 [C.] |
| Acetonitrile | 81.48 [C.] |
| Water | 100.02 [C.] |
| Ethanol (55 mol %)/Acetonitrile (45 mol %) | 72.8 [C.] |
| Ethanol (49 mol %)/Acetonitrile (44 mol %)/Water (7 mol %) | 72.7 [C.] |
| Ethanol (91 mol %)/Water (9 mol %) | 78.2 [C.] |
| Acetonitrile (68 mol %)/Water (32 mol %) | 76.7 [C.] |

The distillation step is conducted with a reflux ratio of at least about 20:1. As used herein, reflux ratio is the ratio of the rate of condensate returned to the distillation column (e.g. from the reflux stream) to the rate of condensate taken off (e.g. from the distillate stream) (by mass), so for example a ratio of 20:1 indicates 20 parts condensate returned to 1 part taken off. The reflux ratios herein may be calculated on a mass basis. Advantageously, the reflux ratio may be in the range of from about 20:1 to about 5000:1, preferably from about 100:1 to about 2000:1 and more preferably from about 500:1 to about 1500:1.

Also advantageously, the distillation step may be carried out at a pressure of from about 0.02 bara to less than about 2 bara, preferably from about 0.05 bara to about 1.5 bara, more preferably from about 0.1 bara to about 1.0 bara and even more preferably from about 0.2 bara to about 0.6 bara. The Applicants have surprisingly found that the azeotrope is maintained at reduced pressure and accordingly that, if desired, a distillation column with fewer stages may be used for the distillation step along with (if reboiler steam is being used) lower grade reboiler steam, which improves overall process efficiency. However, it is also preferable to operate within the pressure limits specified above in order to limit or avoid the need to use refrigerant (depending upon the environment in which the process is being conducted) in the overhead stream to condense and optionally cool the reflux liquid to the column. The temperature of the distillation is consistent with the pressure selected.

Accordingly, in operating the distillation step according to the present invention, the skilled person may select a suitable combination of reflux ratio, number of separation stages, location of the feed point and the state of the feed, i.e. liquid, heated liquid, vapour/liquid mixture, vapour or superheated vapour, in order to obtain desired levels of ethanol recovery and contaminant (e.g. acetonitrile) separation. For example, the reflux ratio may be in the range of from about 100:1 to about 1500:1 by mass, with between about 5 and about 50 ideal separation stages, with a feed point located in about the middle of the column and with the feed heated to approximately match the temperature of the liquid in the column at the feed point.

In some preferred embodiments of the invention, the treated ethanol feedstock (i.e. the bottom stream from the distillation) has a nitrogen content of less than about 2 ppmw, more preferably less than about 1 ppmw, still more preferably less than about 0.5 ppmw, still more preferably less than about 0.25 ppmw, such as less than about 0.1 ppmw or less than about 0.05 ppmw (50 parts per billion by weight, ppbw).

A further advantage offered is that the distillation according to the present invention also acts to de-gas the ethanol feedstock, removing non-condensable gas components such as oxygen, carbon dioxide, carbon monoxide and nitrogen which can negatively impact the final product specification, for example by contaminating a product ethylene stream from an acid-catalysed dehydration of ethanol.

The distillation step may in principle occur at any stage after an ethanol feedstock is provided. For example, it may be an integral part of an ethanol or bio-ethanol production process. Bio-ethanol production processes typically form a mash stream (approximately 10% mash in water) which is fed to a mash column to remove solids and water and then a rectifying column to remove water. An optional drying step after rectifying may also be present, such as for example a molecular sieve or extractive distillation with ethylene glycol or another suitable material. The distillation step may therefore be placed between the rectifying column and drying step or after the drying step. Advantageously, the distillation step is separate to ethanol production, i.e. in the case of bio-ethanol production the distillation step occurs after the rectifying step in order to reduce the energy required to be provided to the distillation.

The distillation step may be a composite step, i.e. a step comprising multiple distillations. Such a step of multiple distillations may comprise one or more distillations according to the present invention and may or may not be in combination with one or more further distillation steps having differing conditions, for example in order to target the removal of other contaminants besides the nitrogen-containing contaminants particularly addressed by the present invention. Where multiple distillations are used, there may or may not be other process steps between them, for example a distillation step may be followed by an adsorption step and then a further distillation step, a distillation step described below (with reference to FIG. 1) including the reboiler may be followed by another such distillation step with or without the reboiler, or a distillation step may be directly followed by another distillation step. It would be recognised by one skilled in the art which stream should pass from one distillation step to the next in order to continue purifying the ethanol feedstock.

Further processing steps may appear as part of the present process after the distillation step and before the acid-catalysed reaction step. For example, acid-catalysed reactions of ethanol are often performed in the vapour phase. Accordingly, as the treated ethanol stream from the distillation step of the present invention is the bottom stream from the distillation column and may therefore be in the liquid phase, it may be desirable to evaporate the bottom stream before reacting it in the presence of an acid catalyst. It may also be desirable to change the pressure of the bottom stream from the distillation column or pass it through a liquid or vapour-phase guard bed. Accordingly, the treated ethanol feedstock resulting from the distillation may be fully or partially condensed and/or evaporated prior to feeding to the acid-catalysed reaction step of the process of the invention.

Following distillation, the bottom stream (i.e. treated ethanol feedstock) is reacted in the presence of an acid catalyst to form a product. The acid catalysed reaction may be any reaction available, for example esterification or dehydration. Preferably, the acid catalysed reaction is a dehydration reaction, e.g. the dehydration of ethanol to ethylene and/or diethyl ether. Often, ethylene is the preferred product of such reactions.

Typically, acid-catalysed reactions of ethanol such as ethanol dehydration processes are performed in the vapour phase, therefore the treated ethanol feedstock may conveniently pass from the distillation (e.g. a distillation column) to the acid-catalysed reaction (e.g. a catalytic reactor) via a reboiler/evaporator to bring the treated ethanol into the vapour phase.

Preferably, in the process according to the invention, the treated ethanol feedstock is in the vapour phase when it contacts the acid catalyst (e.g. dehydration catalyst). This may be achieved by vaporising the treated ethanol feedstock prior to vapour phase acid-catalysed reaction (e.g. ethanol dehydration). The temperature and pressure of the acid-catalysed reaction step may be greater or lower than the temperature and pressure of the treated ethanol feedstock resulting from the distillation step of the process according to the invention, thus the temperature and pressure of the treated ethanol feedstock may be adjusted prior to contacting the treated ethanol feedstock with the acid catalyst; alternatively, the temperature and pressure of the acid-catalysed reaction step in the present invention may be selected such that the treated ethanol feedstock resultant from the distillation step is at the same temperature and pressure as the acid-catalysed reaction step.

The reaction of the ethanol is acid-catalysed. In principle, any acid or mixture of acids may be the catalyst for the further reaction. Advantageously, the acid is suitable for use in heterogeneous catalysis. Examples of acid catalysts include inorganic acids such as tungstic acid, sulphuric acid, phosphoric acid, hydrochloric acid and mixtures thereof. Preferably, the acid catalyst comprises, or is, a heteropolyacid, for example silicotungstic acid, silicomolybdic acid, phosphotungstic acid or phosphomolybdic acid. More preferably, the acid catalyst comprises, or is, silicotungstic acid.

In some embodiments, the acid catalyst is an alcohol dehydration catalyst, such as an ethanol dehydration catalyst, and as such may be any of the alcohol dehydration catalysts or ethanol dehydration catalysts that are known in the art. For example, the acid catalyst may be, or comprise, a silicate, such as a crystalline silicate or zeolite, and may preferably be a crystalline silicate having a Si:Al ratio of at least 100, a dealuminated crystalline silicate or a phosphorous modified zeolite, for example as described in WO 2009/098262, the contents of which are incorporated herein by reference. Alternatively, the acid catalyst may be a heteropolyacid catalyst, for instance as described by WO 2008/138775 and WO 2008/062157, the contents of which are incorporated herein by reference. In preferred embodiments, the acid catalyst is a heteropolyacid catalyst. The heteropolyacid catalyst (advantageously silicotungstic acid) is preferably supported on a suitable inert support, such as silica or alumina.

Suitable conditions for acid-catalysed reactions of ethanol, (for example the dehydration of ethanol) are well-known in the art and to the skilled person, for instance with reference to the prior art documents cited herein. However, in the case of an acidic crystalline silicate, alumina, silica-alumina, zeolite (or mixtures thereof) catalyst, typical reaction conditions include a temperature of from about 280° C. to about 500° C., a total pressure of from about 0.5 bara to about 30 bara, and a partial pressure of alcohol (or ethanol) that is preferably from about 1.2 bara to about 4 bara. In the case of a heteropolyacid catalyst, typical reaction conditions include a temperature of from about 180° C. to about 270° C. and a pressure of from about 1 bara to about 45 bara.

An olefin product may be recovered and may subsequently be used in a wide range of industrial applications as known in the art, for instance in the preparation of polymers and oligomers (and/or precursors thereof), as components of fuels and lubricants and in the preparation of surfactants.

In further embodiments, therefore, the present invention may provide a polymeric product obtained by polymerisation of olefins produced according to the processes of the present invention, an oligomeric product obtained by oligomerisation of olefins produced according to the invention, fuel and lubricant compositions comprising said olefins and/or said oligomeric or polymeric products, and surfactant compositions comprising said olefins and/or said oligomeric or polymeric products.

In some embodiments, the ethanol feedstock may be subjected to additional treatment steps to lower or manage the levels of one or more specified or unspecified nitrogen-containing or other contaminants, such as treatment with an adsorbent material (e.g. in a liquid or vapour phase guard bed) or any of the other techniques known in the art and/or referenced herein, such as disclosed in WO1997/045392, EP1176132A1 or U.S. Pat. No. 6,770,790. Such additional steps may appear before and/or after the distillation step according to the present process, or in between distillation steps if multiple distillation steps are used.

If used, the adsorbent which may be used for the treatment of the ethanol feedstock in the liquid or vapour phase (or in each phase in turn) may be any adsorbent capable of adsorbing nitrogen-containing compounds and that is stable under the conditions at which the ethanol feedstock is brought into contact with it. Preferably, the adsorbent used for the treatment of the ethanol feedstock is a porous solid acidic adsorbent. Examples of suitable adsorbent materials include aluminosilicates such as zeolites, silica-alumina; silicates; silicas; aluminates; aluminas such as activated aluminas; molecular sieves; carbon-based adsorbent materials such as activated carbons (particularly for liquid phase usage); clays (particularly for liquid phase usage); resins, for example strong acid ion exchange resins such as sulphonic acid resin; and aluminophosphates. Particularly for vapour phase usage, the adsorbent may optionally be treated or impregnated with an acid, such as phosphoric acid, phosphonic acid, sulfuric acid or a sulphonic acid, and/or may optionally be modified with a transition metal. Preferably, the adsorbent is selected from the group consisting of zeolites, silica-aluminas and mixtures thereof. The adsorbent material may be used individually or in admixture with other adsorbent materials and/or inert materials, and so for example an adsorption step may be carried out in both the liquid phase and the vapour phase with either adsorption step preceding the other.

The temperature, pressure and space velocities at which the ethanol feedstock contacts the adsorbent may be selected to be suitable for the phase of the ethanol feedstock desired and adsorbent material used.

The adsorption may be carried out by passing the ethanol feedstock in the vapour phase through a fixed bed, fluidised bed or moving bed of the adsorbent. Typically, liquid phase adsorption may be carried out through a fixed bed. Multiple adsorption zones may also be used in this step, wherein each adsorption zone may contain the same or different adsorbents and may be operated at the same or different conditions. One particular example of the use of multiple adsorption zones comprises treating the ethanol feedstock in a system comprising at least two adsorption zones, wherein at least one adsorption zone is operating under conditions such that the ethanol feedstock is contacted with an adsorbent in the liquid phase and at least one adsorption zone is operating under conditions such that the alcohol composition is contacted with an adsorbent in the vapour phase.

Any steps within the processes of the present invention (and/or the process as a whole) may be operated as continuous or batch process, preferably as continuous processes.

With reference now to FIG. 1, a schematic of a process according to the present invention is provided, wherein an ethanol feedstock in feed stream 101 is provided to a distillation column 201. The feed stream 101 may be heated, e.g. to match the temperature of the liquid in the column at the feed point. The distillation column forms at least an overhead stream 102 and a bottom stream 103, each having a respective exit point. The bottom stream may be greater than about 95% of the feed mass rate, preferably from about 98% to about 99.9999% of the feed mass rate. The feed point for the ethanol feedstock may be positioned intermediate between the exit points of the overhead stream 102 and the bottom stream 103. The overhead stream 102 is passed to a condenser 202 (which may be any type of condenser e.g. a conventional condenser as known in the art) forming a condensed stream 104 and a gaseous stream 105. At least a portion (reflux stream 106) of the condensed stream 104 is recycled into the distillation column 201 to provide reflux liquid to the column. The remainder (distillate stream 107) may be passed to further steps 203 (not shown schematically), for example other uses (e.g. as fuel-grade ethanol) or disposal as waste. The reflux ratio is therefore the ratio of the rate of reflux stream 106 returned to the distillation column 201 to the rate of distillate stream 107 taken off to further steps 203. The distillate stream 107 may be very small, for example less than about 5% of the feed mass rate, preferably from about 0.0001% to about 2% of the feed mass rate. The gaseous stream 105 may be disposed of as waste or otherwise captured 204 (not shown schematically), for example by optionally passing the gaseous stream to a vent condenser to minimise the release of volatile organic compounds to the atmosphere. The bottom stream 103 is the treated ethanol feedstock. Bottom stream 103 may be passed to an optional reboiler 205 resulting in an evaporated stream 108 and a product stream 109. The evaporated stream 108 may be recycled into the distillation column 201 to provide vapour and heat to the distillation column 201. The product stream 109 may be passed to the acid-catalysed reaction according to the present invention (206, not shown schematically) directly or via further processing steps (e.g. as detailed herein). Alternatively, bottom stream 103 may be passed to the acid-catalysed reaction step directly or via further processing steps, for example those highlighted herein.

The distillation column can offer improved energy efficiency by heat exchanging the product stream 109 with the feed stream 101. Other heat integration options with upstream and downstream processes could be considered. Examples include, but are not limited to:

- The use of a spare heat source to preheat the feed stream 101, e.g. spare heat from an upstream or downstream process relative to the distillation step
- The use of a spare heat source as reboiler utility
- The use of the product stream 109 as a heat source in a heat exchange with another stream, such as the feed stream 101
- The use of flash steam (generated from high pressure condensate) as reboiler utility In a second aspect, the present invention relates to a process for the preparation of an ethanol feedstock for the acid-catalysed dehydration of ethanol to ethylene, the process comprising the step of distilling an ethanol feedstock comprising at least one nitrogen-containing contaminant wherein the distillation has a reflux ratio of at least 20:1, especially wherein the ethanol feedstock exits the distilling step in a bottom stream.

In a third aspect, the present invention provides a use of a process according to the first aspect to react (e.g. dehydrate) a nitrogen-containing contaminant-depleted, preferably acetonitrile-depleted, ethanol feedstock in the presence of an acid catalyst. The present invention also provides a use of a process according to the first aspect to dehydrate a non-condensable gas depleted, preferably an oxygen, carbon dioxide, carbon monoxide and/or nitrogen depleted, ethanol feedstock in the presence of an acid catalyst.

In a fourth aspect, the present invention provides products obtainable from, preferably obtained from, a process according to the first or second aspect, especially a product comprising ethylene and/or diethyl ether in respect of the first aspect and a product comprising ethanol in respect of the second aspect.

EXAMPLES

A series of batch distillations according to the present invention were carried out upon examples 1-5 below.

| Example | Details |
|---------|---------|
| 1 | 100 wt % bio-ethanol[1] |
| 2 | 98 wt % bio-ethanol[1]/2 wt % water |
| 3 | 95.5 wt % bio-ethanol[1]/4.5 wt % water |
| 4 | bio-ethanol[1] with 100 ppm acetic acid |
| 5 | 95.5 wt % bio-ethanol[1]/4.5 wt % water with 100 ppm acetic acid |

[1]Bio-ethanol sample contained 8.5 ppm nitrogen by mass of which 850 ppb was acetonitrile.

In all cases, a 2 L, three-necked, round bottom flask was used as the reservoir, with 20 trays (10 theoretical stages) of 1" diameter glassware making up the distillation column. A thermocouple was placed in the reservoir and at the take-off point to allow temperature measurement at both places. The take-off point itself had a hold-up volume of ca. 10 mL, filled by closing a Young's tap on a bypass. This was left open, except immediately before (i.e. 2-3 minutes before) samples were collected off the top. The reservoir was charged with the example to be studied and a sample of this example taken. A heating mantle (520 W) contacting the reservoir was put on full power and the distillation apparatus left until the column was refluxing vigorously. It was then left for a further one hour before a series of 5 mL samples were collected from the top of the column at 10 minute intervals. The column was then switched off after one hour (including the time taking samples) and, once cool, a final sample taken from the reservoir. The samples were analysed by gas chromatography with a nitrogen phosphorous detector and trace analyses. It was determined by modelling the conditions above that the distillation operated with a reflux ratio of approximately 120:1.

| | Concentration of Acetonitrile (ppb) | | | | | |
|---|---|---|---|---|---|---|
| | Reservoir | | Column (time following one hour of vigorous refluxing) | | | |
| Example | Start | Finish | 0 min | 10 min | 20 min | 30 min | 40 min |
| 1 | 945 | 215 | 49500 | 33500 | 27300 | 21750 | 17300 |
| 2 | 875 | 155 | 62930 | 21930 | 16700 | 12775 | 9810 |
| 3 | 820 | 215 | 41645 | 26870 | 23160 | 17535 | 13985 |
| 4 | 965 | 155 | 42800 | 31010 | 26245 | 18985 | 14335 |
| 5 | 900 | 35 | 47470 | 26020 | 21860 | 16690 | 12910 |

The results clearly show the effectiveness of the distillation according to the present invention at removing nitrogen-containing contaminant from an ethanol feedstock.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope and spirit of this invention

The invention claimed is:

1. A process for the acid-catalysed dehydration of ethanol, the process comprising the steps of:
   (a) distilling an ethanol feedstock comprising acetonitrile contaminant to form an overhead stream comprising acetonitrile and a bottom stream comprising ethanol, wherein the distillation has a reflux ratio of at least 100:1; and
   (b) reacting the bottom stream in the presence of an acid catalyst to form a product stream comprising ethylene and/or diethyl ether, thereby dehydrating the ethanol.

2. The process according to claim 1, wherein the step of distilling the ethanol feedstock is carried out at a reflux ratio of from 100:1 to 5000:1.

3. The process according to claim 1, wherein the step of distilling the ethanol feedstock is carried out at a pressure of from 0.02 bara to less than 2 bara.

4. The process according to claim 1, further comprising the step of passing the bottom stream to a reboiler to form an evaporated stream and a product stream wherein the product stream replaces the bottom stream in step (b).

5. The process according to claim 4 wherein at least a portion of the evaporated stream is recycled to step (a).

6. The process according to claim 1, wherein the ethanol feedstock is introduced to step (a) at a position intermediate between positions at which the overhead stream and the bottom stream exit step (a).

7. The process according to claim 1, further comprising the step of adding water to the ethanol feedstock before step (a).

8. The process according to claim 1, wherein the acid catalyst comprises silicotungstic acid.

9. The process according to claim 1, wherein the acid catalyst comprises a silicate.

10. The process according to claim 1, wherein the ethanol feedstock is a bio-ethanol feedstock.

11. The process according to claim 1, further comprising the step of contacting the ethanol feedstock with an adsorbent wherein the ethanol feedstock is in a liquid or vapour phase.

12. A process for the preparation of an ethanol feedstock for the acid-catalysed dehydration of ethanol to ethylene, the process comprising the step of distilling an ethanol feedstock comprising acetonitrile contaminant wherein the distillation has a reflux ratio of at least 100:1 and the ethanol feedstock exits the distilling step in a bottom stream and the acetonitrile in an overhead stream.

13. The process according to claim 1 wherein the ethanol feedstock is an acetonitrile-depleted ethanol feedstock.

14. The process according to claim 1, wherein the step of distilling the ethanol feedstock is carried out at a reflux ratio of from 100:1 to 2000:1.

15. The process according to claim 1, wherein the step of distilling the ethanol feedstock is carried out at a reflux ratio of from 500:1 to 1500:1.

16. The process according to claim 1, wherein the step of distilling the ethanol feedstock is carried out at a pressure of from 0.05 bara to 1.5 bara.

17. The process according to claim 1, wherein the step of distilling the ethanol feedstock is carried out at a pressure of from 0.1 bara to 1.0 bara.

18. The process according to claim 1, wherein the step of distilling the ethanol feedstock is carried out at a pressure of from 0.2 bara to 0.6 bara.

19. The process according to claim 1, further comprising the step of adding water to the ethanol feedstock before step (a) in an amount from 0.01% to 5% by weight of the ethanol feedstock.

20. The process according to claim 1, further comprising the step of adding water to the ethanol feedstock before step (a) in an amount from 0.5% to 4% by weight of the ethanol feedstock.

21. The process according to claim 1, further comprising the step of adding water to the ethanol feedstock before step (a) in an amount from 1% to 3% by weight of the ethanol feedstock.

22. The process according to claim 1, further comprising the step of adding water to the ethanol feedstock before step (a) in an amount from 1.5% to 2.5% by weight of the ethanol feedstock.

23. The process according to claim 1, wherein the acid catalyst comprises a crystalline silicate or zeolite.

24. The process according to claim 1, wherein the acid catalyst comprises a crystalline silicate having a Si:Al ratio of at least 100, a dealuminated crystalline silicate or a phosphorous modified zeolite.

25. The process according to claim 1, further comprising the step of contacting the ethanol feedstock with an adsorbent wherein the ethanol feedstock is in the liquid phase.

* * * * *